US007473227B2

(12) United States Patent
Hsu et al.

(10) Patent No.: US 7,473,227 B2
(45) Date of Patent: Jan. 6, 2009

(54) APPARATUS FOR THE TREATMENT OF SLEEP APNEA

(75) Inventors: William Hsu, West Linn, OR (US);
Mark Johnson, Aurora, OR (US);
Gerlad Czygan, Erlangen (DE)

(73) Assignee: Biotronik GmbH & Co.KG, Berlin (DE)

( * ) Notice: Subject to any disclaimer, the term of this patent is extended or adjusted under 35 U.S.C. 154(b) by 634 days.

(21) Appl. No.: 10/932,923

(22) Filed: Sep. 2, 2004

(65) Prior Publication Data
US 2005/0101833 A1 May 12, 2005

(30) Foreign Application Priority Data
Oct. 2, 2003 (DE) ................. 103 47 294

(51) Int. Cl.
*A61B 5/02* (2006.01)
(52) U.S. Cl. ................... 600/483; 600/481; 600/326
(58) Field of Classification Search ................. 600/483, 600/481, 328, 529, 532, 533, 593; 607/11, 607/17, 18, 20, 30, 42, 62
See application file for complete search history.

(56) References Cited
U.S. PATENT DOCUMENTS

| 4,846,195 A | 7/1989 | Alt |
| 4,869,251 A | 9/1989 | Lekholm et al. |
| 4,926,863 A | 5/1990 | Alt |

(Continued)

FOREIGN PATENT DOCUMENTS
DE 697 12 369 11/2002

(Continued)

OTHER PUBLICATIONS

St. Judes Medical, Inc., "St. Jude Medical Begins Evaluation of New Therapy for Sleep Apnea in Pacemaker Patients: First Patient Enrolled in Multicenter Breathe Clinical Trial," News Release—Oct. 29, 2002.

(Continued)

*Primary Examiner*—Chieh M Fan
*Assistant Examiner*—Anita Saidi
(74) *Attorney, Agent, or Firm*—Hahn Loeser & Parks LLP; John J. Cunniff

(57) ABSTRACT

The invention concerns a medical device for implantation in a body, comprising a stimulation unit, a sleep detector unit having at least one signal input which is adapted to detect a sleep condition of the body and to produce a sleep signal, an apnea detector unit which is adapted to detect sleep apnea in dependence on at least one body signal caused by the body and to produce an apnea signal, a therapy unit which is at least indirectly connected to the stimulation unit! the sleep detector unit and to the apnea detector unit and which is adapted to produce, in dependence on the apnea signal and the sleep signal, at least one apnea therapy signal which represents therapy information for preventing and/or for the treatment of sleep apnea, and to send same to the stimulation unit. The medical device has a position sensor, which is operatively connected to the signal input of the sleep detector unit and adapted in dependence on its inclination about at least one spatial axis extending through the position sensor in relation to the horizontal to alter at least one of its electrical properties.

20 Claims, 4 Drawing Sheets

U.S. PATENT DOCUMENTS

| | | | |
|---|---|---|---|
| 5,174,287 A | | 12/1992 | Kallok et al. |
| 5,562,711 A | | 10/1996 | Yerich et al. |
| 6,083,248 A | | 7/2000 | Thompson |
| 6,126,611 A | * | 10/2000 | Bourgeois et al. ............ 600/529 |
| 6,321,122 B1 | * | 11/2001 | Scheiner et al. ............. 607/122 |
| 6,361,508 B1 | * | 3/2002 | Johnson et al. ............. 600/595 |
| 6,392,591 B1 | * | 5/2002 | Hsu et al. ............. 342/357.06 |
| 6,449,503 B1 | * | 9/2002 | Hsu ............................ 600/518 |
| 6,549,925 B1 | * | 4/2003 | Amrany et al. .............. 708/404 |
| 6,556,862 B2 | * | 4/2003 | Hsu et al. ....................... 607/4 |
| 6,574,507 B1 | | 6/2003 | Bonnet |
| 2001/0012954 A1 | * | 8/2001 | Czygan et al. ................. 607/11 |
| 2002/0072775 A1 | * | 6/2002 | Hsu et al. ....................... 607/9 |
| 2002/0193839 A1 | * | 12/2002 | Cho et al. ..................... 607/17 |
| 2002/0193939 A1 | | 12/2002 | Matsuo |
| 2003/0130589 A1 | | 7/2003 | Poezevera |
| 2003/0153953 A1 | | 8/2003 | Park et al. |

FOREIGN PATENT DOCUMENTS

| | | |
|---|---|---|
| DE | 695 26 767 | 1/2003 |
| EP | 0 515 319 A2 | 11/1992 |
| EP | 0940155 B1 | 4/2004 |
| WO | WO 96/30080 | 10/1996 |

OTHER PUBLICATIONS

Garrigue, et al, "Benefit of Atrial Pacing in Sleep Apnea Syndrome," The New England Journal of Medicine, vol. 346 (No. 6), p. 404-412, (Feb. 7, 2002).

* cited by examiner

APPARATUS FOR THE TREATMENT OF SLEEP APNEA

This invention relates to medical devices for the treatment or prevention of sleep apnea. More particularly, this invention relates to medical devices for apnea therapy that impose a low amount of restriction on the patient.

BACKGROUND OF THE ART

A significant proportion of the population is affected by respiratory disturbances. One such respiratory disturbance, is for example, sleep apnea, a temporary cessation of breathing. The most frequent occurence is obstructive sleep apnea, which affects approximately 6% of the male population over the age of 40 years. In obstructive sleep apnea, the upper air passages collapse and close, thereby preventing respiration air from passing. That can occur repeatedly in sleep.

Another form of sleep apnea is the central sleep apnea syndrome. With that syndrome, the breathing passages remain open but central control of the breathing muscles is detrimentally affected. While that form of apnea is observed in between about 10 and 20% of all persons suffering from sleep apnea, it has a high prevalence in patients suffering from cardiac insufficiency. Such patients also frequently have Cheyne-Stokes breathing, which is a periodic decrease and increase in respiration amplitude, also referred to as respiration depth. In that case, the patient has periods of reduced respiration depth, that is to say central apnea, and periods of increased respiration depth, also referred to as hyperventilation. The heart rate, hemodynamics and blood pressure are influenced by those respiration malfunctions. For example, the apnea periods can stimulate an increase in sympathetic activity, which can adversely affect the heart. The concurrence of sleep apnea with cardiac insufficiency substantially reduces the quality of life and capability of the patient. It is therefore essential that in such cases, sleep apnea is monitored, identified and treated.

In general terms, respiration malfunctions such as for example, sleep apnea, require continuous monitoring of a patient and if possible, continuous treatment, rather than only during a stay in a medical institution. In order to monitor and treat that malfunction, the patient has to be monitored and treated while asleep at home. Devices from the prior art include the use of externally applied respiration sensors and respiration masks. With those devices, sleep apnea is treated by artificial respiration devices, which control respiration and enforce inspiration and expiration. In actual fact, those devices involve a significant restriction in terms of quality of life. As that therapy depends on the co-operation of the patient, the imposing nature of that device could prevent its on-going use.

The article "Benefit of Atrial Pacing in Sleep Apnea Syndrome" by Garrigue et al, which appeared in the New England Journal of Medicine (Vol 346, No 6, pages 404-412, Feb. 7, 2002), describes a study conducted on a patient group which already had implanted cardiac pacemakers for the treatment of sinus bradycardia by means of atrial superstimulation. Based on some reports of these patients that they had fewer respiration difficulties after the implantation procedure, 15 patients were selected for investigation in a succession of nights. During the tests the implanted pacemaker was programmed to either not stimulate the heart at all or to place the heart continuously. During the stimulus phase, atrial superstimulation was set at about 15 beats per minute above the average heart rate of the patient at night. In the case of 13 out of 15 patients, the observed apnea-hypopnea index fell by more than 50% during the nights with continuous dual-chamber stimulus by the cardiac pacemaker. The apnea-hypopnea index is a measurement of the frequency of the skipped or slowed respiration rate at night. The reason for the observed improvement is not referred to, but it was possible to improve both obstructive and central apnea by means of the pacemaker equipment.

At the end of the year 2003, the St Jude Medical Center announced a new study relating to evaluation of pacemaker therapy for sleep apnea. As in the case of the Garrigue study, the plan is to assess the influence of an increased pacemaker rate during rest, but the study is evidently restricted to cardiac pacemaker patients with diagnosed sleep apnea. Evidently, the St Jude study seeks to use a secret algorithm for downloading into the cardiac pacemaker of a patient.

The use of the heartbeat volume as an input parameter is known in pacemaker therapy, for adjusting or adapting the pacemaker rate. A respiration volume value is calculated from the frequency and the relative amplitude of a reference signal, which can be determined from a measurement of an intrathoracal impedance. Evidently, the St Jude algorithm uses a time-of-day clock for switching the pacemaker therapy on and off. It will be appreciated that an algorithm based on time-of-day clock readings can cause problems if the patient travels across time zones, when there are changes in time (as for daylight savings time) and if the patient has a disruption in the normal sleep schedule.

SUMMARY OF THE INVENTION

Therefore, an aspect of the present invention is to provide a device for the treatment of sleep apnea by means of overcontrolled stimulus of the atrium of a heart by means of an implanted cardiac pacemaker.

That aspect is attained by a medical device as set forth herein, which has a position sensor operatively connected to the sleep detector and which is adapted in dependence on its inclination about at least one spatial axis extending through the position sensor in relation to the horizontal, to alter at least one of its electrical properties.

The invention concerns a medical device for implantation in a body, comprising a stimulation unit which is adapted to produce an electrical stimulation pulse in dependence on an apnea therapy signal, and a sleep detector unit having at least one signal input, which is adapted to detect a sleep condition of the body in dependence on at least one input signal and to produce a sleep signal which corresponds to a sleep detection event. The medical device for implantation in a body, referred to hereinafter also as an implantable medical device, also has an apnea detector unit which is adapted to detect sleep apnea in dependence on at least one body signal caused by the body and to produce an apnea signal which corresponds to an apnea detection event. The implantable medical device also has a therapy unit which is at least indirectly connected to the sleep detector unit and to the apnea detector unit and which is adapted to produce, in dependence on the apnea signal and the sleep signal, at least one apnea therapy signal which represents therapy information selectively for the prevention of sleep apnea, for the treatment of sleep apnea or both, and to send same to the stimulation unit.

Such a system has a particular advantage for patients in respect of whom cardiac pacemaker implantation is already appropriate. Such a system can also be advantageous for patients who suffer from sleep apnea without there being other indications for an implantation procedure.

DETAILED DESCRIPTION OF THE INVENTION

Figure 1:
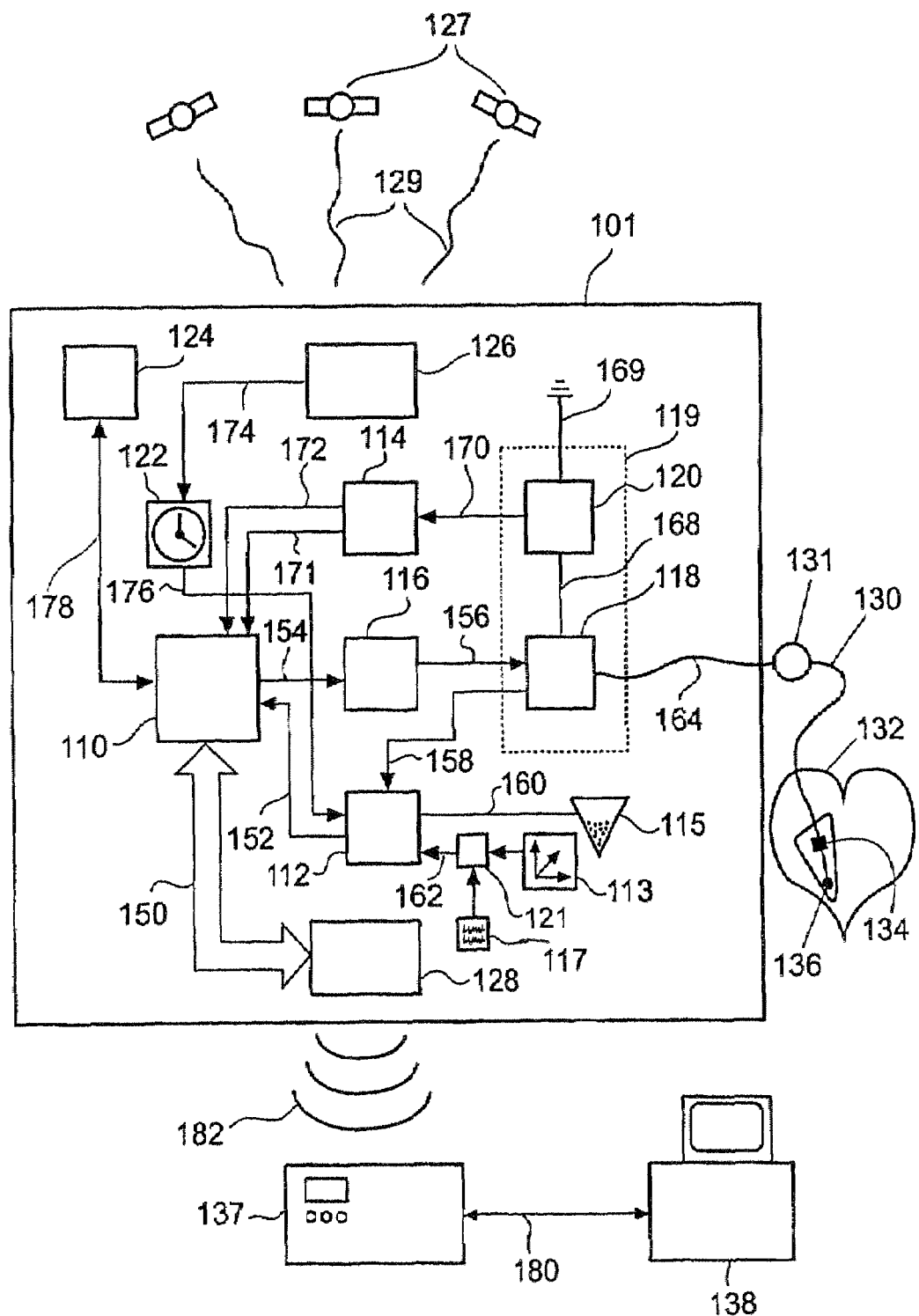
FIG. 1 diagrammatically shows an embodiment of the implantable medical device the co-operation of the features thereof and its effect with devices in its surroundings, FIG. 2 diagrammatically shows elements of the sleep detector unit and the apnea detector unit together with sensors in a signal configuration diagram.

In a preferred embodiment, the apnea detector unit includes an apnea weighting discriminator with at least one input for a body signal. The apnea weighting discriminator is adapted to assess the body signal in accordance with a predetermined apnea weighting function and to produce an apnea signal representative of sleep apnea.

The sleep detector unit preferably includes a sleep weighting discriminator with at least one input for an input signal, wherein the sleep weighting discriminator is adapted in accordance with a predetermined sleep weighting function, to assess the input signal and to produce a sleep signal representative of a sleep condition.

Further, the sleep weighting discriminator and/or the apnea weighting discriminator may include fuzzy logic.

The medical device preferably includes a time-of-day clock, which is connected to the sleep detector unit and is thus available as an input parameter for deciding whether there is a sleep status or not.

In a particular embodiment, the medical device has a world time zone detector with a satellite receiver, wherein the world time zone detector is operatively connected to the time-of-day clock and is adapted to receive satellite signals, to ascertain a position on the Earth by evaluation of the satellite signals and to produce a world time zone signal on the basis of the position on the Earth and to send said signal to the time-of-day clock which is adapted to suitably correct the time of day.

For example, the satellite receiving system can determine the position in the form of co-ordinates. On the basis of the co-ordinates, the satellite receiving system can make an association into a world time zone in which the wearer of the medical device is at the present time. The satellite receiving system is preferably connected to the time-of-day clock and can thus implement a correction to the time of day if the wearer of the medical device is in a different time zone. In that way it is advantageously possible to ensure, in a simple fashion, that the wearer of the medical device, when traveling through various world time zones, is not involved with therapy at the wrong time if a therapy procedure is to be implemented in dependence on a time of day. Preferably, the satellite receiving system includes the Global Positioning System (GPS) known from the state of the art.

The stimulation unit is adapted to produce an electrical stimulation pulse, which is suitable for stimulating tissue in such a way that a depolarization threshold for a muscle contraction is exceeded.

In an embodiment, the stimulation unit has a respiration musculature stimulation unit, which is adapted to produce an electrical stimulation pulse for stimulation of the diaphragm or the thorax musculature. In this embodiment, the implantable medical device has an output for the connection of respiration musculature stimulation electrodes.

In a preferred embodiment, the implantable medical device has a cardiac pacemaker or defibrillator. In this embodiment, the therapy unit can be connected to the cardiac pacemaker or defibrillator and send therapy signals containing stimulation information thereto. The cardiac pacemaker is thus an implementing means for providing therapy for sleep apnea.

An embodiment of an activity sensor is an acceleration sensor or a closed loop stimulation (CLS).

A rest or load condition of the body is derived in closed loop stimulation from an intracardial impedance signal. That technology is discussed in the article "Closed Loop stimulation—Ein neues Herzschrittmacher—Konzept zur Frequenzadaption mittels eines Kontraktilitätssensors" in the Journal Kardiol, 1999, Vol 6, Iss 1, pages 21-25.

In a preferred embodiment, the implantable medical device has a sensor for detecting intracardial impedance, which is connected to the sleep detector and is adapted on the basis of intracardial impedance to detect when the body is at rest and to produce a rest condition signal representative of the rest condition of the body. The sensor for detecting intracardial impedance can also be in the form of a contractility sensor.

In the case of devices with CLS, the medical device can advantageously also use the intracardial impedance sensor of the CLS in order to branch an intracardial impedance signal from the CLS.

An acceleration sensor can advantageously be in the form of a triaxial acceleration sensor, in which the directional axes of the accelerations which can be detected form an orthogonal system and which is operatively connected to the sleep detector and adapted to produce an acceleration time signal representative of an acceleration.

By virtue of that arrangement, a body movement can be evaluated in such a way that, upon evaluation of the time signals of the acceleration sensor, on the basis of acceleration directions which preferably occur, the implantable medical device can distinguish between normal day movement situations and, for example, rolling movements during a sleep period.

In this embodiment, the implantable medical device preferably has an acceleration pattern classifier, which is adapted to distinguish body movements during sleep from those during a time-of-day situation on the basis of predetermined acceleration patterns, which can be respectively stored for all three axes of movement.

In this embodiment, the acceleration pattern classifier is connected on the output side to the sleep detector unit and on the input side to the acceleration sensor and is adapted to evaluate an acceleration time signal and to recognise predetermined acceleration patterns in the acceleration time signal, to classify them and to produce an acceleration pattern signal representative of an acceleration pattern and to output said signal at the output side.

As an alternative to an acceleration sensor, the medical device may also have a speed sensor.

The acceleration patterns provided for classification purposes can be time signals or power spectra. In the case of the power spectra, the acceleration pattern classifier has at the input side an FFT analyzer (FFT: Fast-Fourier-Transformation) which is adapted to continuously produce acceleration pattern power spectra from an acceleration time signal and to send said acceleration pattern power spectra to the acceleration pattern classifier. Storage of power spectra for classification comparison is advantageously particularly sparing in terms of using storage space, in comparison with the storage of time signals.

In a preferred embodiment, the implantable medical device has a time-of-day clock, which is connected to the sleep detector unit.

In a further preferred feature, in addition to the time-of-day clock, the implantable medical device has at least one activity sensor in order to increase the degree of accuracy of recognition as to whether a sleep has begun or ended and whether a stimulation therapy procedure is to be started or terminated.

In order to activate the stimulation algorithm of the present invention, which means switching the stimulation protocol to "on," the algorithm requires that the time-of-day clock must show that the time is in a predetermined time interval for sleeping and that at least one activity sensor indicates the absence of a movement on the part of the patient.

An obvious matter of concern is the capability of the patient to fall asleep, when the stimulation protocol is turned on, and this can happen when the protocol is activated by the above-indicated conditions. In that case, the stimulation protocol signifies an increase in the heart rate. In that situation, many embodiments of the present invention can provide an increase in the stimulation rate with a rising edge over a period of between 10 and 30 minutes. In a preferred embodiment, by way of example, an overall increase in the stimulation rate of 10 beats per minute can be afforded by a rise in the stimulation rate of one beat per minute over 10 minutes.

The sleep algorithm of the present invention can set the stimulation protocol to "off" when the predetermined time interval is reached and a movement is detected by at least one activity sensor. Just as a preferred sleep algorithm can increase the stimulation rate in accordance with a ramp function when the stimulation protocol is switched on, the preferred sleep algorithm can also reduce the stimulation rate to a similar absolute rate. If for example, the stimulation rate upon being switched on increases by one beat per minute, the reduction should also be one beat per minute upon terminating the procedure.

If there is more than just one activity sensor, a plurality of algorithms are provided for recognizing whether a "NO MOVEMENT status" is reached. Otherwise positive recognition of the "NO MOVEMENT status" of one of the above-mentioned sensing means is sufficient. In a further preferred third algorithm, it is possible to allocate to each of the various sensing means a respective weighting factor and the predominance of "NO MOVEMENT" weighted signals, which can be sufficient.

In each of the sleep algorithms of the present invention, the possibility of extracorporeally programming the rise/fall in the stimulation rate and the predetermined sleep time period is considered to be essential.

In some embodiments of the present invention, the algorithm also reads the respiration pattern of the patient by way of the signal form of minute ventilation or the closed loop stimulation (CLS) signal form in order to detect sleep apnea. In that embodiment, stimulation can be switched to "on" only by way of recognition of sleep apnea.

In some further embodiments, there is a simple position detector, in which case the status of the position detector can be used in a part of the sleep algorithm in order to detect whether a sleep situation has begun.

An implantable monitoring system of the present invention goes beyond all limits of previously known systems. The system can monitor respiration and send respiration information with other diagnostic data to a remote monitoring center. In that way, a physician is in a position to monitor the patient without continuously observing the patient. The respiration monitor can be integrated into a therapeutic device which is an implantable pacemaker or a defibrillator (ICD, ICD: Implantable Cardioverter/Defibrillator), or it can operate as a stand-alone diagnostic device.

Respiration is measured by way of intrathoracal impedance.

Monitoring can be combined with various therapeutic means. For example, sleep apnea therapy can be incorporated into a resynchronization therapy using a cardiac pacemaker or defibrillator (ICD) for patients with cardiac insufficiency.

The implantable respiration monitor includes means for measuring impedance, a means for long distance telemetry (LDT), means for the storage of data, means for measuring a cardiac action signal and a central control unit. Many of the monitors may also include an electrotherapeutic module such as a cardiac pacemaker, a defibrillator (ICD) or both.

In an embodiment, the means for measuring impedance may inject a sub-stimulus threshold electrical current between two electrodes which are selected by the available lines. The current can comprise bi-phase pulses of constant amplitude. A pair of electrodes can be used for measuring a voltage.

In that case, the measured voltage is proportional to the impedance of the tissue in the measurement region. In some embodiments, the current and voltage electrodes are the same electrodes. Prior to analog-digital conversion, the voltage is amplified and filtered. A band pass filter is preferred for that purpose. The filter can be so selected that the respiration signal passes but higher and lower frequency components are attenuated.

The medical device preferably has an oxygen sensor which is connected to the apnea detector unit and adapted to determine a level of oxygen concentration in the blood and to produce a blood oxygen signal representative of the level of blood oxygen concentration. The level of oxygen concentration in the blood thus serves as an input value for the apnea detector unit.

In an embodiment, the implantable medical device has a respiration minute volume detection unit which is connected to the apnea detector unit. Preferably, the respiration minute volume detection unit includes means for determining thoracal impedance.

In order to detect respiration, it is necessary to ascertain the thoracal impedance. The impedance of the thorax varies during the respiration cycles because the electrical conductivity of the lungs changes in accordance with a differing air content. The thoracal impedance also changes in accordance with geometrical alterations.

A preferred embodiment of a detector for thoracal impedance is a tripolar measuring configuration which uses the housing or the casing of the implant as a common electrode for current and voltage. A current is injected between the casing and a ring electrode of the right ventricular line or the left ventricular line. The resulting voltage is measured between the electrode tip and the casing so that the impedance of the thoracal tissue is measured. A line for stimulation of the left ventricle, either a coronary sinus line or an epicardial line, can also be used with the corresponding tripolar configuration. In that case, the left-hand part of the lung is contained in the measuring region. In some embodiments, it is also possible to use a defibrillator line (ICD line), including the stimulus coil, for impedance measurement procedures.

In an embodiment, the medical device has a heart beat volume detection unit, which is connected to the sleep detector unit, and/or the therapy unit and is adapted to determine a heartbeat volume and to produce a heartbeat volume signal representative of the heartbeat volume.

The heartbeat volume can thus serve as an input parameter for sleep detection or as an actual condition parameter for the therapy unit for regulating the heartbeat volume.

In a preferred embodiment, the position sensor includes at least two switching contacts and at least one electrically conductive ball, which is arranged in such a way as to electrically conductively connect or separate the switching contacts in dependence on the inclination of the position sensor. The electrically conductive balls are preferably metal balls.

As an alternative thereto, instead of the metal balls, a position sensor may also include carbon balls. Preferably, the carbon balls contain compressed activated carbon dust, and further preferably additionally a binding agent. The advantage of using the activated carbon balls is that the number of carbon balls involved in the short-circuit depends on the positional angle of the position sensor with respect to the horizontal. That arrangement affords a differing electrical resistance between the contacts of the position sensor in dependence on the angular position. Alternatively, to achieve the same effect as that of the carbon balls, it is also possible to use a ball material involving a predetermined ohmic resistance. Preferably, such balls are plastic material balls or glass balls which are vapor-deposited with a thin metal layer. The conductivity of the metal layer can be adjusted by way of the layer thickness and the textural properties.

The position sensor can also be a Hall probe, which is adapted to produce a Hall voltage in dependence on its orientation in the magnetic field of the Earth.

As an alternative to that embodiment of the position sensor, a position sensor in accordance with the invention can also be a mercury switch, which is known from the state of the art.

The remote observation system that is used with the present invention is known from the state of the art. The implant can send diagnostic data by way of the long distance telemetry means (LDTM) to a device outside the patient, typically a device which is positioned laterally of the bed of a patient. From there the data are sent to a central service center where a physician can access the data.

The respiration signal of a patient affords many parameters, which can be extracted for diagnostic purposes. Those data are stored in the implant and can be sent in a compressed form. The stored values can also be interrogated by the physician with an external device. The external device can display the received data on a display in the form of numbers, trends, histograms or the like. For remote monitoring, the data are compressed into long-term mean values, numerical values and so forth, which are sent, for example, every 24 hours to a service center or on another regular basis. In addition, the device can be equipped in such a way that the patient is allowed to implement a transmission. The intended device according to the invention can also be fitted with threshold switches, based on various possible alarm criteria.

Various diagnostic parameters can be extracted from the respiration signal and stored as apnea statistical information. These can be the following parameters, without being limited thereto:

Respiration frequency: respiration minute volume (relative to a reference value); count value of the pauses in respiration (or the apnea events); duration of the pauses in respiration; counters for the hyperventilation phases; duration of the hyperventilation phases; classification of the respiration phases (normal, obstructive apnea, central apnea, hyperventilation, Cheyne-Stokes breathing). Monitoring of lung edemas is also possible.

Cardiac action signals detected by the implant can also be correlated with the respiration signals. That is particularly important in terms of monitoring central sleep apnea and for patients with cardiac insufficiency who suffer from sleep apnea. Some of the heart signal data can include the heart rate, event counters and so forth but are not restricted thereto. Variations in the heart rate can prove to be particularly useful in connection with respiration data, since it is known that obstructive sleep apnea is frequently accompanied by alternating phases of bradycardia and tachycardia. Diagnostic functionality of the implant can be combined with therapeutic options, for example atrial overstimulation. The respiration sensor can trigger a pace control therapy procedure if an apnea was detected.

The device can also be used as a therapy monitor. Long-term success or short-term success with the pacemaker therapy can be monitored. In addition it is possible to use a drug therapy corresponding to a respiration malfunction in conjunction with the implant.

The invention will now be described in greater detail with reference to Figures. FIG. 1 shows an implantable medical device 101 comprising a central control unit 110, a sleep detector unit 112, an apnea detector unit 114, a pacemaker unit 118 and an impedance sensor 120. The implantable medical device 101 also has a stimulation electrode output 131 which is connected by way of a connecting line 164 to the pacemaker unit 118. FIG. 1 also shows a heart 132, an electrode line 130 which passes into the right atrium of the heart 132 and to the distal end region of which is mounted a ring electrode 134 and a tip electrode 136.

To detect an intrathoracal impedance, the impedance sensor 120 is adapted to cause a current to flow between the housing of the implantable medical device 101 and the ring electrode 134 and to detect a voltage resulting therefrom between the housing and the tip electrode 136. For that purpose, the impedance sensor 120 is connected by way of a housing line 169 to the housing of the implantable medical device 101 and is connected to the pacemaker unit 118 by way of a connecting line 168, the pacemaker unit 118 being adapted during an interruption in stimulation to provide an electrical connection between the impedance sensor 120 and the ring electrode 134 and the tip electrode 136 when the electrode line 130 is connected to the stimulation output 131 of the implantable medical device 101.

The apnea detector unit 114 is connected to the impedance sensor 120 by way of a connecting line 170 and is adapted to evaluate the variation in respect of time of an intrathoracal impedance signal detected by the impedance sensor 120 and to produce therefrom a respiration signal, to evaluate said respiration signal in accordance with the variation in respect of time thereof, and to produce a corresponding evaluation result which, for example, contains the information relating to pauses in respiration.

As the output signal, the apnea detector unit 114 can produce an apnea detector signal which represents the evaluation result for example, in the form of an item of apnea status information and an item of apnea therapy information, and can send it to the central control unit 110. For that purpose, the apnea detector unit 114 is connected at the output side by way of a connecting line 172 to the central control unit 110. The apnea detector unit 114 is also connected to the central control unit 110 for the transmission of items of apnea statistics information by way of a connecting line 171 and is adapted to produce a statistical evaluation result of the respiration signal and to send an apnea statistics signal representative of the evaluation result to the central control unit 110 by way of the connecting line 171.

The apnea statistics signal can include the following parameters:

| | |
|---|---|
| Respiration frequency: | trend, histogram, minimum, maximum, mean value, respiration amplitude; |
| Respiration minute ventilation: | trend, histogram, minimum, maximum, mean value; |
| Apnea events: | absolute number, number per night; |
| Duration of the apnea events: | trend, histogram, minimum, maximum, mean value, total during one night; |
| Number of hyperventilation phases: | absolute number, number per night; |
| Classification of the respiration phases: | normal respiration, obstructive apnea, central apnea, hyperventilation, Cheyne-Stokes breathing. |

The central control unit 110 is, for example, in the form of a programmable microprocessor and can execute a control program that is implemented therein.

The sleep detector unit 112 is adapted on the input side to receive signals by way of the connecting lines 158, 160, 162 and 176, to evaluate same, to produce a sleep signal corresponding to the evaluation result and to send same at the output side to the central control unit 110 by way of the connecting line 152.

The sleep detector unit 112 is connected at the input side by way of a heart rate connecting line 158 to the pacemaker unit 118 which, at the output side, produces a heart rate signal corresponding to a detected heart rate and can send it to the sleep detector unit 112 byway of the connecting line 158.

The sleep detector unit 112 is connected at the input side by way of a connecting line 160 to a position sensor 115, which is adapted, in dependence on its angular position with respect to the horizontal, to change its electrical resistance. The sleep detector unit 112 is adapted to interrogate the angular position of the position sensor 115 and for that purpose to apply an electrical voltage to the position sensor 115 by way of the connecting line 160 and to detect a resulting electrical current.

The sleep detector unit 112 is connected at the input side by way of a connecting line 162 to an acceleration pattern classifier 114 connected to a triaxial acceleration sensor 113. The acceleration pattern classifier 114 is adapted to evaluate a time signal of the triaxial acceleration sensor 113 and to distinguish between various acceleration patterns which correspond to acceleration patterns of a wearer of the implantable medical device 101. For that purpose, the acceleration pattern classifier 114 is connected by way of a connecting line to an acceleration pattern memory unit 117 and is adapted to read therefrom, acceleration patterns which are stored there, and to compare them to the acceleration patterns detected by way of the triaxial acceleration sensor 113 and to classify the detected acceleration patterns. The acceleration pattern classifier 114 can produce an acceleration pattern signal representative of an acceleration pattern and send it by way of the connecting line 162 to the sleep detector unit 112.

The acceleration pattern classifier 114 can have an FFT analyzer, which is adapted to continuously produce a sequence of acceleration pattern power spectra from the time signal of the triaxial acceleration sensor 113. Classification is then effected on the basis of the acceleration pattern power spectra and acceleration pattern power spectra are stored in a predetermined manner in the acceleration pattern memory unit 117.

As an alternative to that embodiment, the acceleration pattern classification procedure can also be effected on the basis of time signals, although it will be noted that this requires markedly more memory space in comparison with the acceleration pattern power spectra.

The sleep detector unit is connected by way of a connecting line 176 to a time-of-day clock 122 which is adapted to produce a time-of-day signal corresponding to a clock time and to send it at the output side to the sleep detector unit by way of the connecting line 176. The time-of-day clock is connected by way of a connecting line 174 to a world time zone detector, which has a satellite receiver, for example a GPS receiver.

The satellite receiver is adapted to receive a satellite signal 129 emitted by satellites 128, to evaluate same and to calculate therefrom an Earth position, for example in the form of co-ordinates. The world time zone detector is adapted, for example, with a look-up table to associate an ascertained Earth position with a world time zone and to produce a world time zone signal and to send that signal at the output side by way of the connecting line 174 to the time-of-day clock 122.

The central control unit 110 is connected to the therapy unit 116 by way of a connecting line 154 and, depending on the respective requirement of a therapy, controlled by the control program, can produce a therapy signal containing an item of therapy information, in dependence on the apnea detector signal received by way of the connecting line 172 and the sleep signal received by way of the connecting line 152, and send that therapy signal to the therapy unit 116 by way of the connecting line 154. The therapy unit 116 is connected to the pacemaker unit 118 by way of a connecting line 156 and is adapted to produce a heart rate demand signal in accordance with the respective therapy required by the central control unit, by way of the connecting line 154 on the basis of the therapy signal and to send the heart rate demand signal by way of the connecting line 156 to the pacemaker unit 118 which can thereupon suitably set the pace rate.

The central control unit 110 is connected to a memory unit 124 by way of a connecting line 178 for the storage of apnea statistical information received for example, by way of the connecting line 171.

The central control unit 110 is connected by way of a bidirectional data bus 150 to a telemetry unit for wireless data transfer (long distance telemetry system) 128. By way of example the telemetry unit 128 is a Bluetooth telemetry unit.

The central control unit 110 can thus send apnea statistical information and heart signal information 182 detected by the pacemaker unit 118 wirelessly to a mobile patient application device 137 by way of the telemetry unit 128. A control program can be received by way of the telemetry unit 128 and sent by way of the bidirectional databus 150 to the central control unit 110 and stored there, and the central control unit 110 and the telemetry unit 128 can be suitably designed for that purpose.

The mobile patient application device 137 can be set up, for example, in the proximity of the bed of a patient. The mobile patient application device 137 is connected to a central service center 138 by way of a network connecting line 180 for the transfer of patient-related data. From the service center, a physician for example, can call up and monitor patient information. As an alternative to the network connecting line 180, the mobile patient application device 137 and the central service center 138 can have a wireless interface, for example a Bluetooth interface, and patient-related data can be transferred wirelessly by way of that Bluetooth interface.

Figure 2:
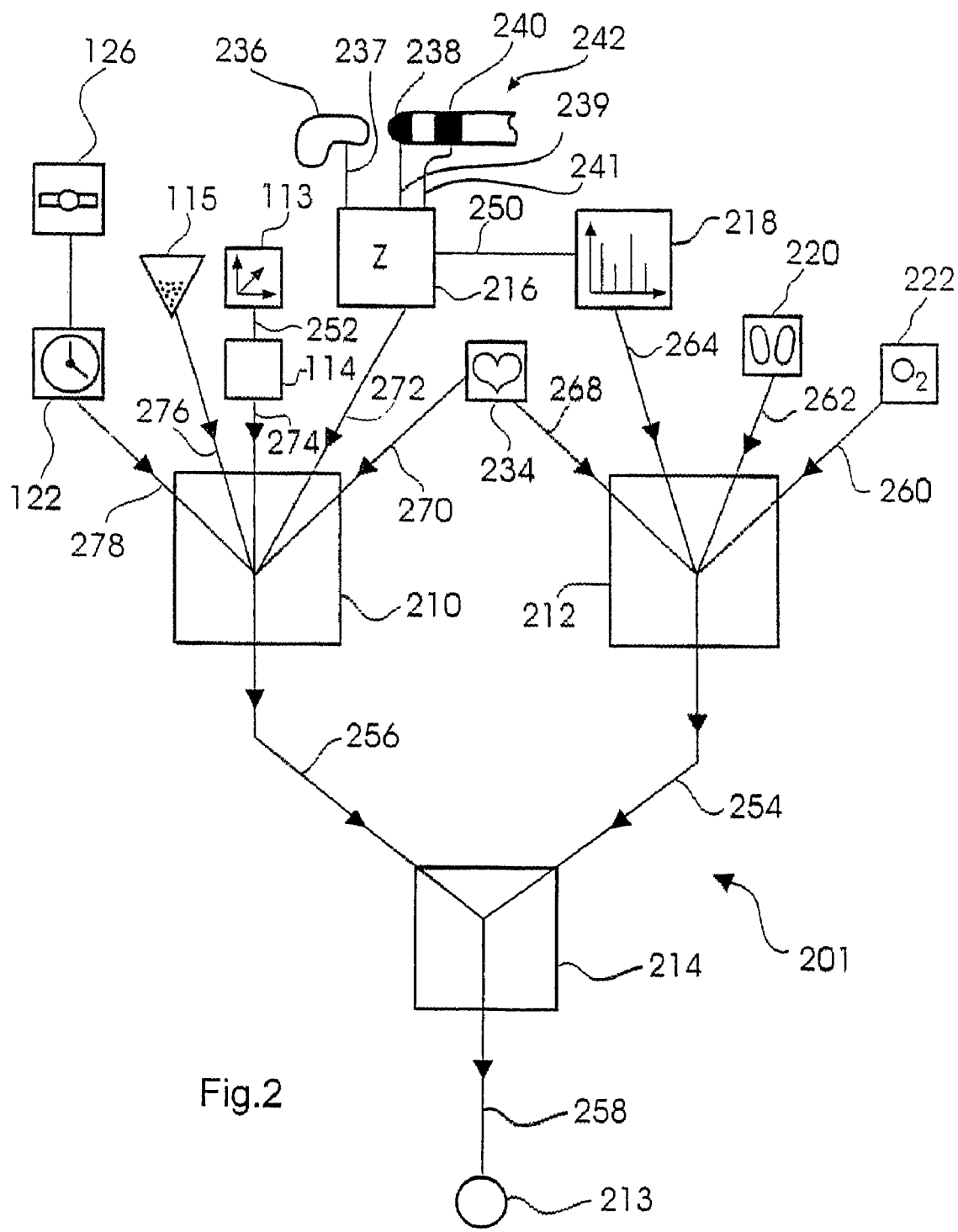

FIG. 2 shows—illustrated diagrammatically—the co-operation of a sleep weighting discriminator 210 which can be contained in the sleep detector unit 112, with an apnea weighting discriminator 212 which can be contained in an apnea detector unit 114.

The sleep weighting discriminator 210 has signal inputs to which sensors or in the broader sense, signal-generating means, are connected by way of connecting lines 270, 272, 274, 276 and 278. The sleep weighting discriminator 210 is adapted to assess the signals at the signal inputs in accordance with a predetermined weighting function and to produce a sleep signal representative of the assessment result and to send the sleep signal at the output side by way of a connecting line 256 to a therapy discriminator 214.

The apnea weighting discriminator 212 also has signal inputs, which are connected to signal-generating means by way of connecting lines 260, 262, 264 and 268. The apnea weighting discriminator 212 assesses the signals at the signal inputs in accordance with a predetermined weighting function and produces an apnea signal and sends that signal at the output side by way of a connecting line 254 connected thereto, to the therapy discriminator 214.

The sleep weighting discriminator 210 is connected by way of a connecting line 270 to a heart rate sensor 234 which can be contained in the pacemaker unit 118. In that way, an actual condition heart rate can be emitted by the heart rate sensor 234 by way of the connecting line 270 and received by the sleep weighting discriminator 210. The sleep weighting discriminator 210 is connected at the input side by way of a connecting line 272 to an impedance sensor 216. The impedance sensor 216 is connected by way of a connecting line 241 to a ring electrode 240 and by way of a connecting line 239 to a tip electrode 238, which electrodes are arranged in the region of the distal end 242 of an electrode line.

The impedance sensor 216 is also connected by way of a connecting line 237 to a housing 236 of the implantable medical device 101 and is adapted to cause a current to flow at the output side by way of the connecting lines 237 and 241 and to detect a resulting voltage at the input side by way of the connecting line 239 and the connecting line 237 and to form an impedance from the detected voltage and the current. The impedance sensor 216 is adapted to calculate an intracardial impedance from that detected impedance and to send an output signal representative of the intracardial impedance to the sleep weighting discriminator 210 by way of the connecting line 272.

An acceleration pattern classifier 114, which has already been described with reference to FIG. 1, is connected by way of a connecting line 252 to a triaxial acceleration sensor 113 and is adapted at the output side to send a signal representative of the classification result to the sleep weighting discriminator 210 by way of the connecting line 274.

The sleep weighting discriminator 210 is also connected at the input side by way of a connecting line 276 to a position sensor 115, as already described with reference to FIG. 1.

A time-of-day clock 122 is connected at the input side to a world time zone detector 126 and is adapted to send at its output side a clock time signal corrected according to a location in the world to the sleep weighting discriminator 210 by way of a connecting line 278.

The apnea weighting discriminator is connected at the input side to a blood oxygen sensor 222 by way of a connecting line 260, at the input side to a respiration minute volume detection unit 220 by way of a connecting line 262 and at the input side to an impedance evaluation unit 218 by way of a connecting line 264.

The impedance evaluation unit 218 is connected to the impedance sensor 216 by way of a connecting line 250 and is adapted to evaluate an impedance time signal of the impedance sensor 216, which characterizes respiration activity, and to produce a respiration signal characterizing the number and duration of pauses in respiration, and to send the respiration signal at the output side to the apnea weighting discriminator 212 by way of the connecting line 264.

The apnea weighting discriminator 212 is connected at the input side to the heart rate sensor 234 by way of a connecting line 268 and can thus receive as an input value a heart rate signal produced by the heart rate sensor.

The apnea weighting discriminator is adapted to produce an apnea signal on the basis of a predetermined apnea weighting function and to send that signal at the output side to the therapy discriminator 214 by way of the connecting line 254.

On the basis of a therapy weighting function, the therapy discriminator assesses the apnea signal available at the input side and the sleep signal available at the input side and associates with the assessment result a therapy result which can be outputted by the therapy discriminator at the output side by way of the connecting line 258 at a discriminator output 213. The therapy unit shown in FIG. 1 can be connected to the discriminator output 213 by way of the connecting line 154.

Figure 3:
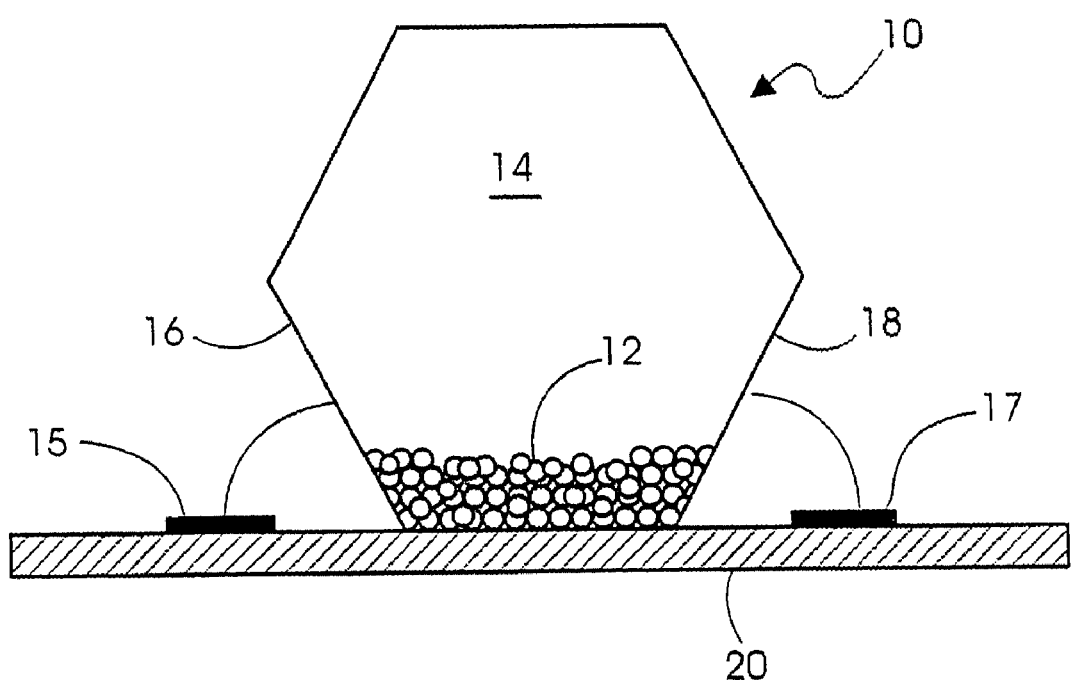
FIG. 3 shows a first embodiment of a position sensor.

As diagrammatically shown in FIG. 3, the position sensor 10 of the present invention can be an object of hexagonal shape with a multiplicity of metal balls 12 contained in an internal hollow space 14. When the patient is lying down, the position sensor 10 is positioned in such a way that the metal balls 12 make an electrical connection between the lower side walls 16 and 18 so that the electrical connection is detected as a short-circuit. When the patient is standing, the balls 12 contact only one of the lower side walls 16 or 18, which is detected as an open circuit. In an embodiment as shown, contact surfaces A and B are disposed on a board 20. Although the connection of the lower side walls 16 and 18 to the contact surfaces is illustrated in the form of wires, there are other known possible ways of making that connection. The side walls can also be provided with a contact surface which is provided to below the base surface of the sensor, thus permitting simple, connecting wire-free soldering of the sensor in a soldering wave bath. It is to be expected that the position sensor is of the size of a 0806 capacitor or a 0603 capacitor. A primary advantage of the position sensor is that it does not consume any energy.

Figure 4:
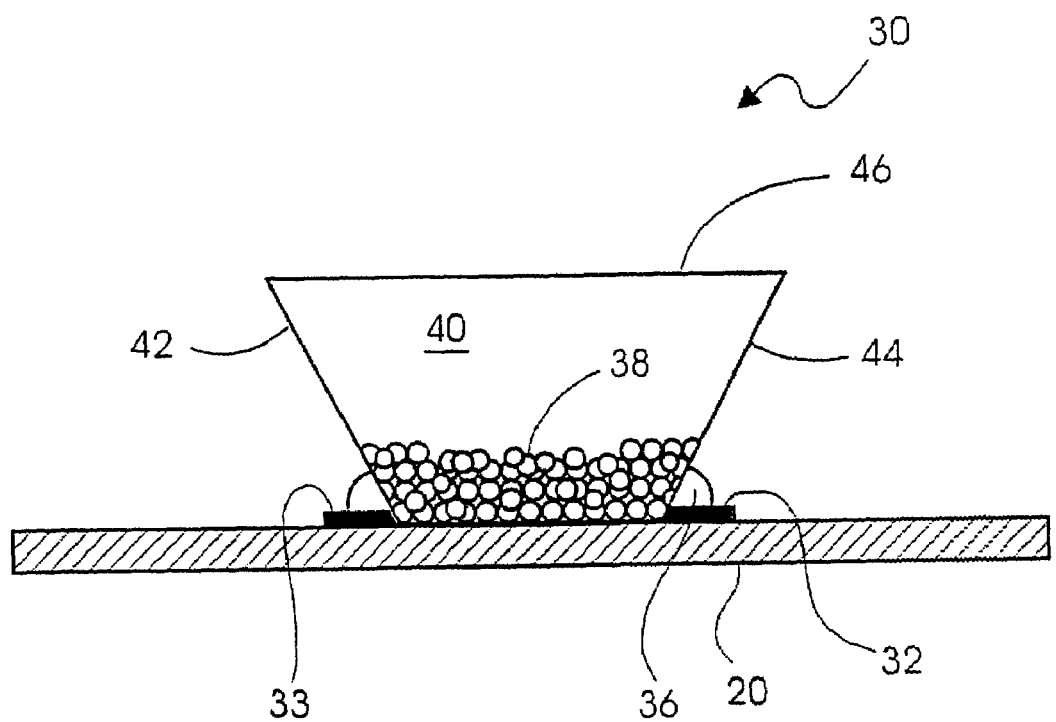
FIG. 4 shows a second embodiment of a position sensor.

FIG. 4 shows a further embodiment of a position sensor 30. The position sensor 30 includes electrically conductive balls 38 disposed in a cavity 40. The cavity 40 is formed by electrically conductive side walls 42 and 43 and by a cover surface 46. Unlike the position sensor shown in FIG. 3, the contact surfaces 42 and 43 are also provided on a portion of the bottom surface, which is afforded for mounting on a board. FIG. 4 also shows contact surfaces of conductor tracks 32 and 33, on to each of which respective ones of the contact surfaces 42 and 44 are soldered with soldering tin 36.

Figure 5:
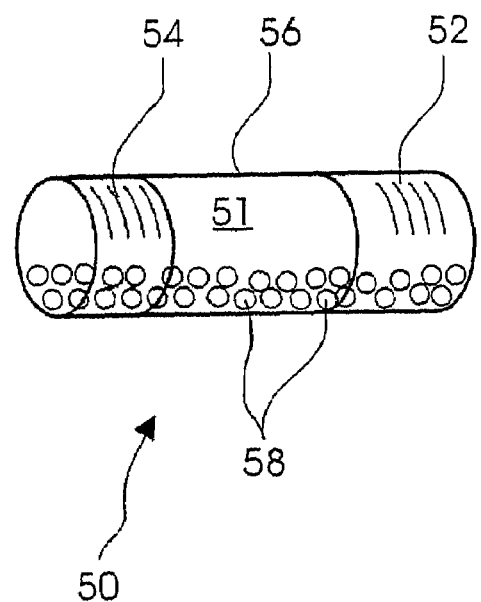
FIG. 5 shows a third embodiment of a position sensor.

FIG. 5 shows an embodiment of a cylindrically shaped position sensor 50 with a hollow space 51 enclosed by a cylindrical wall 56. The cylindrical wall 56 has two electrically conductive ring contacts 54 and 52, which are spaced from each other in the longitudinal axial direction. The hollow space 51 is in part filled with electrically conductive balls 58. When the cylindrical position sensor 50 is disposed with its axial length in horizontal orientation, the electrically conductive ring contacts 52 and 54 are electrically connected together by the electrically conductive balls 58. Depending on the respective level of filling of the hollow space 51 with electrically conductive balls 58, it is possible to set an angle relative to the horizontal, at which the ring contacts 52 and 54 are still—or no longer electrically connected to each other.

If such a cylindrical position sensor 50 is a component part of an implantable medical device and if the longitudinal axis of the cylindrical position sensor 50 is oriented in parallel relationship with the longitudinal axis of the body of a wearer of the implantable medical device, then the electrically conductive ring contacts 52 and 54 are always electrically connected to each other when the wearer of the implantable medical device is in a horizontal position, irrespective of whether the wearer assumes a position of lying on the back, on the stomach or on the side.

In an embodiment (not shown) of a position sensor, an electrically conductive ball is disposed in a hollow space, which is enclosed by a hollow spherical wall. A plurality of electrically conductive contacts is disposed at the inside of the hollow spherical wall. The diameter of the electrically conductive ball in the hollow space and the spacing of the electrically conductive contacts on the inward side of the position sensor wall are such that, in any position of the position sensor, at least two of the electrically conductive contacts are connected together by way of the electrically conductive ball when for example a force due to weight acts on the electrically conductive ball.

We claim:

1. A medical device for implantation in a body, comprising:
   a stimulation unit which is adapted to produce an electrical stimulation pulse in dependence on an apnea therapy signal,
   a sleep detector unit having at least one signal input, which is adapted to detect a sleep condition of the body in dependence on at least one input signal and to produce a sleep signal which corresponds to a sleep detection event,
   an apnea detector unit which is adapted to detect sleep apnea in dependence on at least one body signal caused by the body and to produce an apnea signal which corresponds to an apnea detection event,
   a therapy unit which is at least indirectly connected to the stimulation unit, the sleep detector unit and to the apnea detector unit and which is adapted to produce, in dependence on the apnea signal and the sleep signal, at least one apnea therapy signal which represents therapy information for preventing and/or for the treatment of sleep apnea, and to send same to the stimulation unit,
   wherein the medical device has a position sensor which is operatively connected to the signal input of the sleep detector unit and adapted in dependence on its inclination about at least one spatial axis extending through the position sensor in relation to the horizontal to alter at least one of its electrical properties, and
   wherein the therapy unit is adapted to produce an apnea therapy signal in the form of an increase in the stimulation rate of 10 beats per minute by increasing the stimulation rate by one beat per minute over 10 minutes, thereby providing an apnea therapy signal that reduces a disturbance in sleep in a patient in which the device is implanted.

2. A medical device as set forth in claim 1, characterized in that the apnea detector unit includes an apnea weighting discriminator with at least one input for a body signal, wherein the apnea weighting discriminator is adapted to assess the body signal in accordance with a predetermined apnea weighting function and to produce an apnea signal representative of sleep apnea.

3. A medical device as set forth in claim 1, characterized in that the sleep detector unit includes a sleep weighting discriminator with at least one input for an input signal, wherein the sleep weighting discriminator is adapted in accordance with a predetermined sleep weighting function to assess the input signal and to produce a sleep signal representative of a sleep condition.

4. A medical device as set forth in claim 1, characterized in that the medical device has a sensor for detecting intracardial impedance, which is connected to the sleep detector and adapted to detect resting of the body on the basis of the intracardial impedance and to produce a rest condition signal representative of the rest condition of the body.

5. A medical device as set forth in claim 1, characterized in that the medical device has a respiration minute volume detection unit connected to the apnea detector unit.

6. A medical device as set forth in claim 1, additionally comprising an oxygen sensor which is connected to the apnea detector unit and adapted to determine a level of oxygen concentration in the blood and to produce a blood oxygen signal representative of the level of blood oxygen concentration.

7. A medical device as set forth in claim 1, additionally comprising a heartbeat volume detection unit which is connected to at least one of the sleep detector unit and the therapy unit and is adapted to determine a heartbeat volume and to produce a heartbeat volume signal representative of the heartbeat volume.

8. A medical device as set forth in claim 1, additionally comprising a time-of-day clock which is connected to the sleep detector unit and is adapted to produce a time-of-day signal and to send same to the sleep detector unit.

9. A medical device as set forth in claim 8, characterized in that the medical device has a world time zone detector with a satellite receiver, wherein the world time zone detector is operatively connected to the time-of-day clock and is adapted to receive satellite signals, to ascertain a position on the Earth by evaluation of the satellite signals and to produce a world time zone signal on the basis of the position on the Earth and to send said signal to the time-of-day clock which is adapted to suitably correct the time of day.

10. A medical device as set forth in claim 1, additionally comprising a triaxial acceleration sensor in which the directional axes of the accelerations which can be detected form an orthogonal system and which is operatively connected to the sleep detector unit and adapted to produce an acceleration time signal representative of an acceleration.

11. A medical device as set forth in claim 10, characterized in that the medical device has an acceleration pattern classifier which is connected on the output side to the sleep detector unit and on the input side to the acceleration sensor and is adapted to evaluate an acceleration time signal and to recognize predetermined acceleration patterns in the acceleration time signal, to classify them and to produce an acceleration pattern signal representative of an acceleration pattern and to output said signal.

12. A medical device as set forth in claim 11, characterized in that the acceleration pattern classifier has at the input side an FFT analyzer which is adapted to continuously produce acceleration pattern power spectra from an acceleration time signal and to send said acceleration pattern power spectra to the acceleration pattern classifier.

13. A medical device as set forth in claim 1, characterized in that the position sensor includes at least two switching contacts and at least one electrically conductive ball which is arranged in such a way as to electrically conductively connect or separate the switching contacts in dependence on the inclination of the position sensor.

14. A medical device as set forth in of claim 1, characterized in that the position sensor is a Hall probe which is adapted to produce a Hall voltage in dependence on its orientation in the magnetic field of the Earth.

15. A medical device as set forth in claim 1, characterized in that the stimulation unit is a cardiac pacemaker or defibrillator.

16. A medical device as set forth in claim 1, characterized in that the stimulation unit is a respiration musculature stimulation unit which is adapted to produce an electrical stimulation pulse for stimulation of the diaphragm or the thorax musculature.

17. A home monitoring system comprising an implantable medical device as set forth in claim 1, and a mobile patient application device, wherein the mobile patient application device is connected wirelessly by way of a telemetry unit to the implantable medical device.

18. A patient monitoring system comprising an implantable medical device as set forth in claim 1, and a mobile patient application device connectable wirelessly by way of a telemetry unit to the implantable medical device and a central service center, wherein the central service center is connected at least at times to the mobile patient application device for the data transfer of patient-related data by way of a network connecting line or a wireless connection.

19. A method of treating sleep apnea in a patient, the method comprising implanting a medical device in the patient, the medical device comprising:

a stimulation unit adapted to produce an electrical stimulation pulse in dependence on an apnea therapy signal, a sleep detector unit having at least one signal input, adapted to detect a sleep condition of the body in dependence on at least one input signal and to produce a sleep signal which corresponds to a sleep detection event, an apnea detector unit which is adapted to detect sleep apnea in dependence on at least one body signal caused by the body and to produce an apnea signal which corresponds to an apnea detection event, a therapy unit which is at least indirectly connected to the stimulation unit, the sleep detector unit and to the apnea detector unit and which is adapted to produce, in dependence on the apnea signal and the sleep signal, at least one apnea therapy signal which represents therapy information for preventing and/or for the treatment of sleep apnea, and to send same to the stimulation unit, wherein the medical device has a position sensor which is operatively connected to the signal input of the sleep detector unit and adapted in dependence on its inclination about at least one spatial axis extending through the position sensor in relation to the horizontal to alter at least one of its electrical properties, and producing an apnea therapy signal using the therapy unit, in the form of an increase in the stimulation rate of 10 beats per minute by increasing the stimulation rate by one beat per minute over 10 minutes, thereby providing an apnea therapy signal that reduces a disturbance in sleep in the patient.

20. The method of claim 19, wherein the stimulation unit is a cardiac pacemaker or defibrillator.

\* \* \* \* \*